United States Patent
Dewey et al.

(10) Patent No.: US 8,303,628 B2
(45) Date of Patent: Nov. 6, 2012

(54) SPINAL STABILIZATION SYSTEM

(76) Inventors: Jonathan M. Dewey, Sunnyvale, CA (US); Christopher M. Patterson, Memphis, TN (US)

(*) Notice: Subject to any disclaimer, the term of this patent is extended or adjusted under 35 U.S.C. 154(b) by 673 days.

(21) Appl. No.: 12/120,588

(22) Filed: May 14, 2008

(65) Prior Publication Data

US 2009/0287248 A1 Nov. 19, 2009

(51) Int. Cl.
*A61B 17/70* (2006.01)
*A61B 17/04* (2006.01)

(52) U.S. Cl. .......... 606/246; 606/264; 606/301

(58) Field of Classification Search .......... 606/246, 606/264, 301, 254, 265, 257, 278, 275, 252
See application file for complete search history.

(56) References Cited

U.S. PATENT DOCUMENTS

| | | | | |
|---|---|---|---|---|
| 5,282,863 A * | 2/1994 | Burton | | 606/254 |
| 5,387,212 A * | 2/1995 | Yuan et al. | | 606/264 |
| 5,910,141 A | 6/1999 | Morrison et al. | | |
| 6,440,133 B1 | 8/2002 | Beale et al. | | |
| 6,454,773 B1 | 9/2002 | Sherman et al. | | |
| 6,582,434 B2 | 6/2003 | Kawakami et al. | | |
| 6,660,006 B2 | 12/2003 | Markworth et al. | | |
| 6,749,613 B1 * | 6/2004 | Conchy et al. | | 606/57 |
| 6,790,209 B2 | 9/2004 | Beale et al. | | |
| 6,911,030 B1 | 6/2005 | Vanacker et al. | | |
| 7,066,938 B2 | 6/2006 | Slivka et al. | | |
| 7,083,621 B2 | 8/2006 | Shaolian et al. | | |
| 7,666,211 B2 * | 2/2010 | Perez-Cruet et al. | | 606/250 |
| 7,722,649 B2 * | 5/2010 | Biedermann et al. | | 606/257 |
| 2002/0193793 A1 | 12/2002 | Kawakami et al. | | |
| 2005/0038432 A1 | 2/2005 | Shaolian et al. | | |
| 2006/0247636 A1 | 11/2006 | Yuan et al. | | |
| 2008/0177318 A1 * | 7/2008 | Veldman et al. | | 606/256 |

* cited by examiner

*Primary Examiner* — Pedro Philogene

(57) ABSTRACT

A spinal stabilization system is disclosed. The spinal stabilization system can include at least one anchorage component and a surgical rod. The anchorage component has a superior end, an inferior end, and an axial passage therebetween. The surgical rod is configured to be installed at least partially within the axial passage of the anchorage component. The surgical rod includes an elongate body having a first end and a second end. The first end or the second end is adapted to engage the superior end or the inferior end of the anchorage component. Further, the surgical rod is configured to substantially constrain rotational movement within the anchorage component.

22 Claims, 11 Drawing Sheets

SPINAL STABILIZATION SYSTEM

FIELD OF THE DISCLOSURE

The present disclosure relates generally to orthopedics and orthopedic surgery. More specifically, the present disclosure relates to spinal stabilization systems.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

A spinal stabilization system is disclosed. The spinal stabilization system includes at least one anchorage component having a superior end, an inferior end, and an axial passage therebetween. The spinal stabilization system can also include a surgical rod configured to be installed at least partially within the axial passage of the anchorage component. The surgical rod includes an elongate body having a first end and a second end. The first end or the second end is adapted to engage the superior end or the inferior end of the anchorage component. Further, the surgical rod is configured to substantially constrain rotational movement within the anchorage component.

In another embodiment, a surgical rod that can be installed within a spinal stabilization system is disclosed. The surgical rod includes an elongate body having a distal end and a proximal end. The surgical rod further includes an engagement member perpendicular to the axis of the elongate body. The engagement member is configured to engage an anchorage component and substantially constrain rotational movement within the anchorage component.

In still another embodiment, a method of treating a spine is disclosed and can include installing a first anchorage component having a superior end and an inferior end on a first vertebra and installing a surgical rod within at least a portion of the first anchorage component. The method includes adjusting the surgical rod to engage the superior end or the inferior end of the first anchorage component. The method further includes adjusting the surgical rod to substantially constrain rotational movement of the surgical rod within the first anchorage component.

In yet another embodiment, a kit is disclosed and can include a plurality of anchorage components. The kit further includes a surgical rod configured to be installed within each of the plurality of anchorage components. The surgical rod has an engagement member configured to engage at least one end of each of the plurality of anchorage components and substantially constrain rotational movement of the surgical rod within the anchorage components. Also, the kit can include a plurality of setscrews configured to secure the surgical rod within each of the plurality of anchorage components.

Description of Relevant Anatomy

Figure 1:
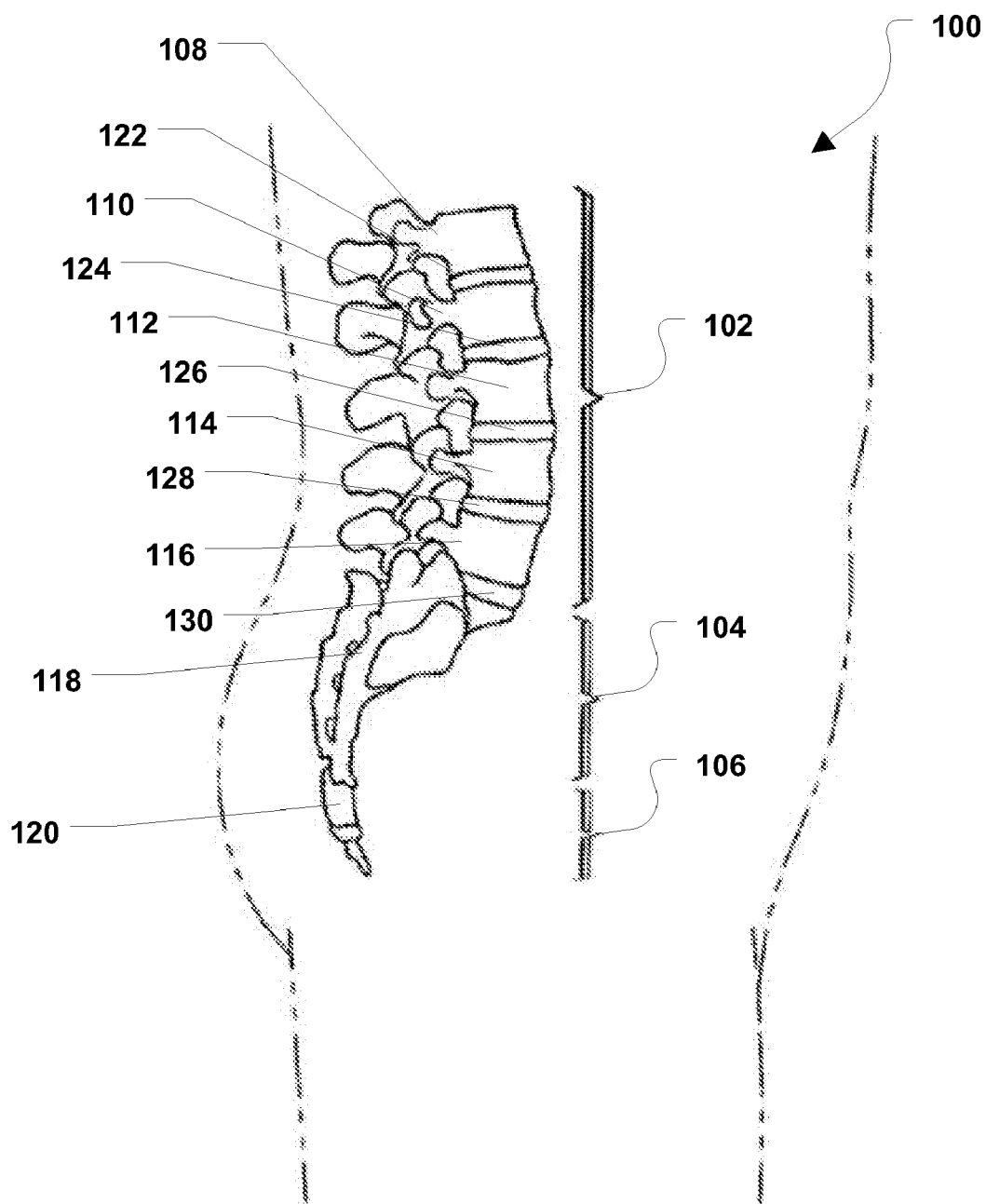
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, treatment of that intervertebral lumbar disc 122, 124, 126, 128, 130 can be effected in accordance with one or more of the embodiments described herein.

Figure 2:
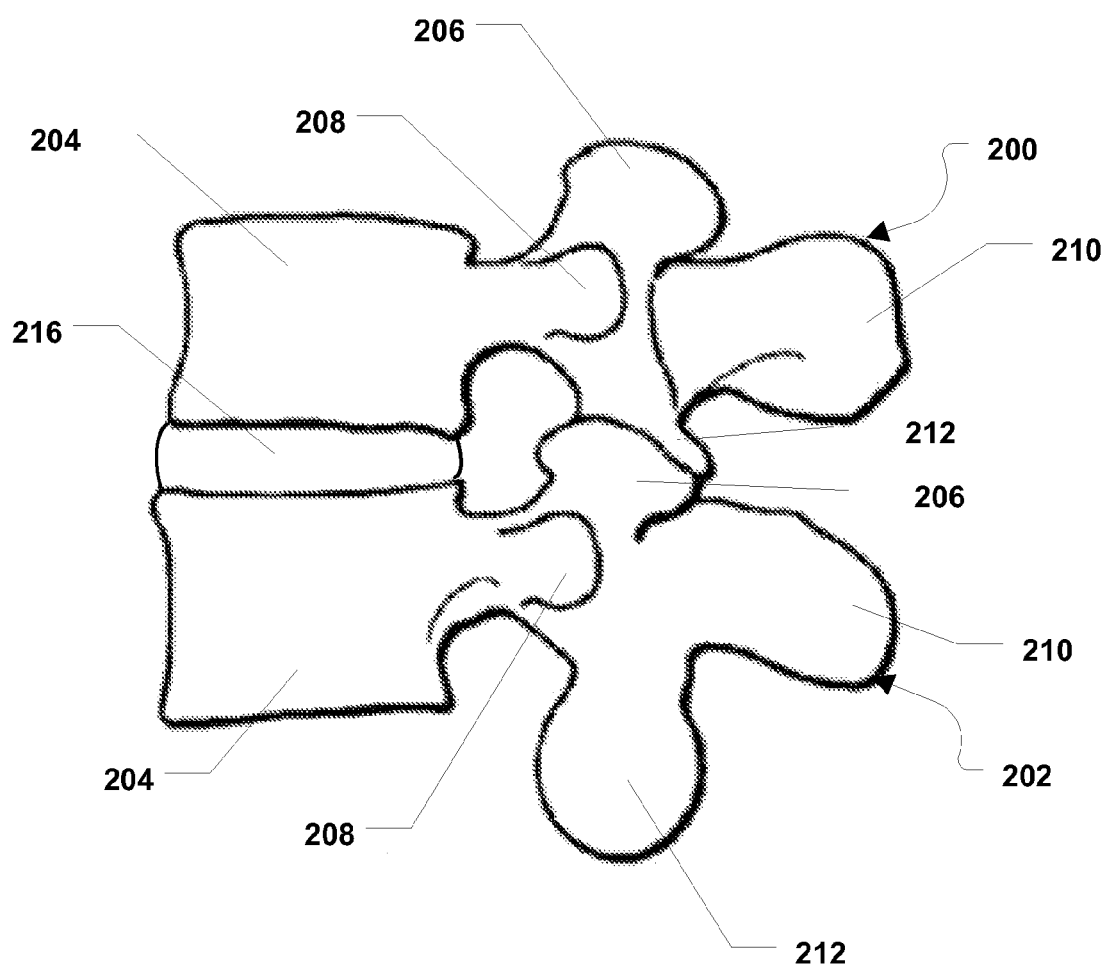
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
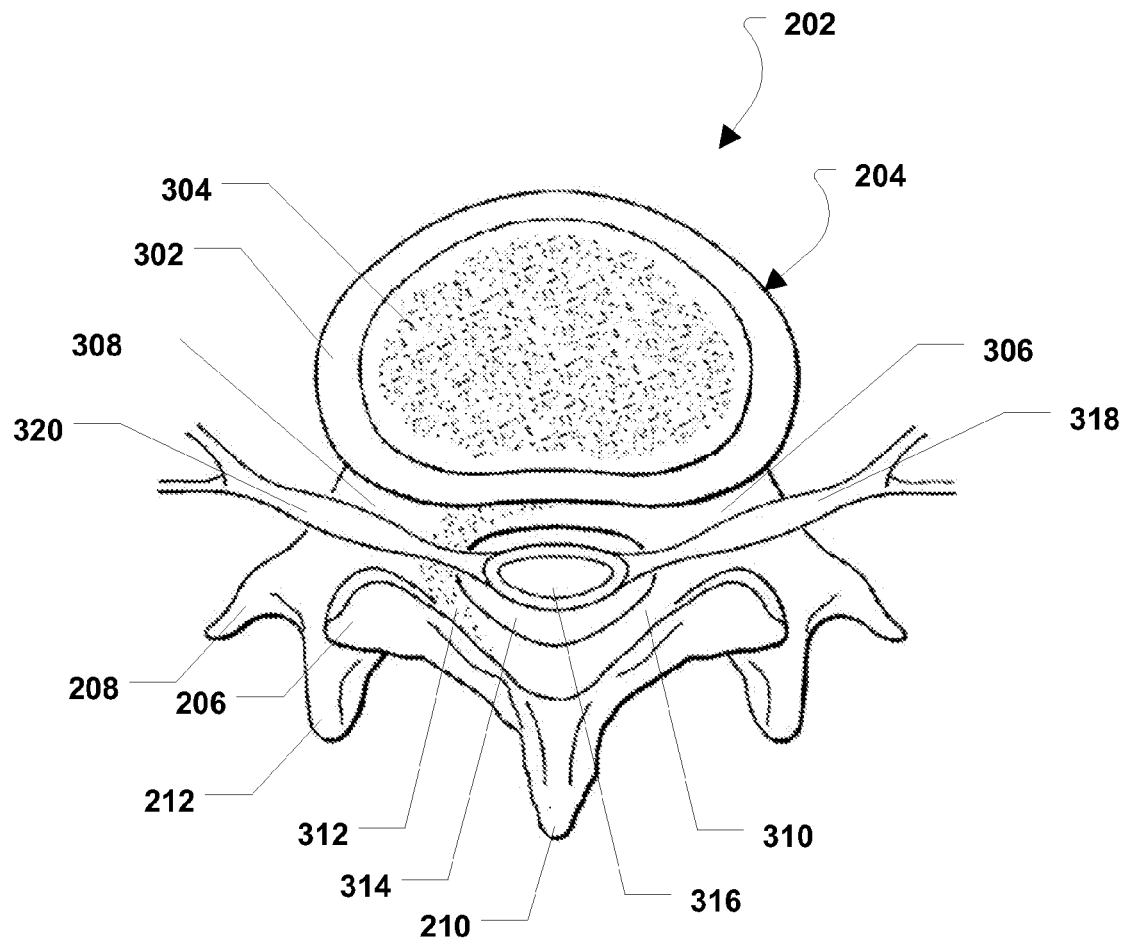
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

In order to correct spinal defects, a spinal stabilization system is typically used. A general embodiment of a spinal stabilization system includes anchorage components attached to the vertebrae and surgical rods transfixed between the anchorage components. Due to the variety of spinal defects and curvatures of the spine, different rotational or translational orientations of the surgical rods within the anchorage components are desired. Multiple embodiments of spinal stabilization systems can be seen in FIGS. 4-15 where the surgical rods are adapted to engage the anchorage components in a specific rotational or translational orientation to support or stabilize the spine.

Description of a First Embodiment of a Spinal Stabilization System

Figure 4:
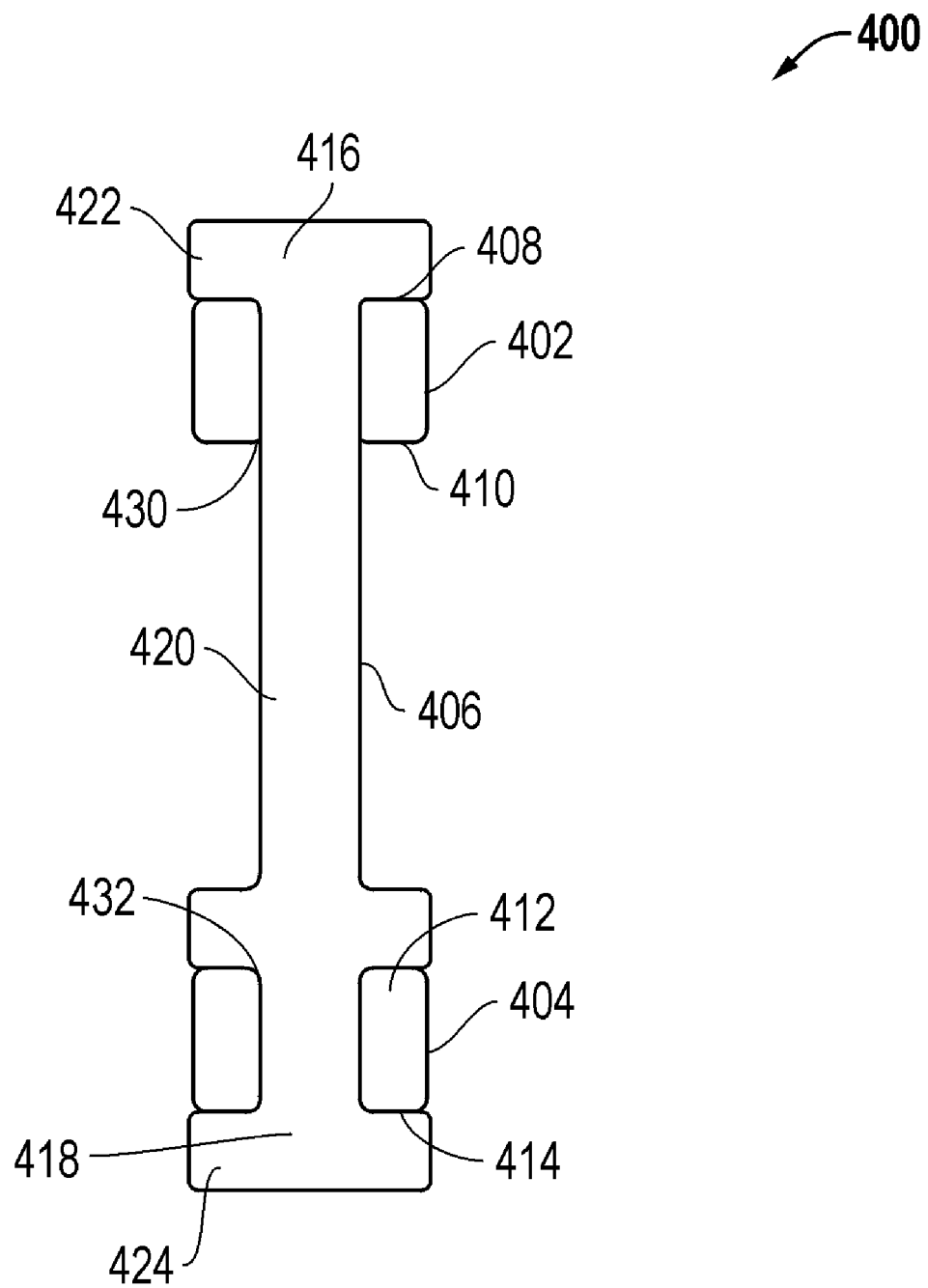
FIG. 4 is a posterior view of a first embodiment of a spinal stabilization system.

Referring to FIG. 4, a first embodiment of a spinal stabilization system is shown and is generally designated 400. As illustrated, the spinal stabilization system 400 can include a first anchorage component 402 and a second anchorage component 404. In one or more alternative embodiments, the spinal stabilization system 400 can include more than two anchorage components or less than two anchorage components. Although generally shown in a horseshoe configuration, the anchorage components 402, 404 may be of any configuration that is sized and shaped to fix to a vertebra and engage a spinal rod 406. As illustrated, anchorage component 402 has a superior end 408 and an inferior end 410 with an axial passage 430 therebetween. Further, anchorage component 404 has a superior end 412 and an inferior end 414 with an axial passage 432 therebetween.

As shown in FIG. 4, spinal stabilization system 400 can include a surgical rod 406. The surgical rod 406 has an elongate body 420. The elongate body 420 can include a first end 416 and a second end 418. FIG. 4 indicates that a surgical rod 406 can extend at least partially through each anchorage component 402, 404. In particular, the surgical rod 406 can extend through an axial passage 430, 432 formed in each respective anchorage component 402, 404. Further, surgical rod 406 is configured to engage the superior end 408, 412 or the inferior end 410, 414 of the anchorage components 402, 404. The surgical rod 406 may be of any suitable configuration to engage the superior end 408, 412 or the inferior end 410, 414 of anchorage components 402, 404 to substantially constrain the rotational movement of the surgical rod 406 within the anchorage component 402, 404. Further, the surgical rod 406 may be of any suitable configuration to engage the superior end 408, 412 or the inferior end 410, 414 of anchorage components 402, 404 to substantially constrain the translational movement of the surgical rod 406 within the anchorage component 402, 404. "Substantially constrain" as used herein refers to preventing the motion of the surgical rod 406 within the anchorage component 402, 404 while allowing motion due to the elasticity of the material.

In a particular embodiment, at least one end 416, 418 of the surgical rod 406 has at least one engagement member 422, 424 that is perpendicular to the axis of the elongate body 420 to engage a respective anchorage component 402, 404. As seen in FIG. 4, the first end 416 of the surgical rod 406 is configured to engage the superior end 408 of the anchorage component 402. Alternatively, the surgical rod 406 may be configured to engage the inferior end 410, 414 of the anchorage component 402, 404. Second end 418 of surgical rod 406 is configured to engage both the superior end 412 and inferior end 414 of anchorage component 404.

The surgical rod 406 can be a bar having a rectangular cross-section. Alternatively, the surgical rod 406 can have a cross-section that is square, round, elliptical, Y-shaped, U-shaped, any polygonal shape, or a combination thereof. Further, the engagement member 422, 424 of the surgical rod 406 can be integrally formed with the surgical rod 406. Alternatively, the engagement member 422, 424 may be formed as separate pieces and fixed to the surgical rod 406, i.e., welded.

In a particular embodiment, the surgical rod 406 can be made from one or more extended use approved medical materials. For example, the materials can be any substantially rigid biocompatible materials such as metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The (PAEK) materials can include polyetherketone (PEK), polyetheretherketone (PEEK), polyetherketoneketone (PEKK), polyetherketoneetherketoneketone (PEKEKK), or a combination thereof. Alternatively, the surgical rod 406 can be made from any other biocompatible material that can withstand a compressible load. In an embodiment, the elongate body 420 of the surgical rod 406 can be a substantially rigid biocompatible material.

In an embodiment, the surgical rod 406 can be made of a shape-memory material. The surgical rod 406 may be partially made of shape-memory material or completely made of shape-memory material. For instance, the engagement member 422, 424 of the surgical rod 406 can be made of shape-memory material. The engagement member 422, 424 can be partially made of a shape-memory material or completely made of a shape-memory material. An exemplary shape-memory material is Nitinol, titanium, or any shape-memory polymers. In an embodiment, shape-memory materials enable the superior end 408, 412 or inferior end 410, 414 of the surgical rod 406 to be form fitted to the complimentary anchorage component 402, 404.

Once the surgical rod 406 is set within the anchorage component 402, 404, the surgical rod 406 can be held in the anchorage component 402, 404 by a fixation component of any suitable configuration (not shown) that extends from each anchorage component 402, 404. In an embodiment, the fixation component allows for translational adjustment of the surgical rod 406. In an embodiment, the fixation component allows for rotational adjustment of the surgical rod 406. In an embodiment, the fixation component irreversibly locks the surgical rod 406 within each respective anchorage component 402, 404. For instance, the fixation component may be a cap, a setscrew, a hoop, or an eyelet. In an embodiment, the hoop allows the surgical rod 406 to slide. In an embodiment, the eyelet is collapsible. In an embodiment, the fixation component is any device that closes the open end of the anchorage component 402, 404 and allows for movement of the rod within the anchorage component 402, 404. In an embodiment, the fixation component is a setscrew where each setscrew can include a break-off head that can be sheared by a break-off tool at a predetermined torque. As such, each setscrew may not be over-torqued.

Description of a Second Embodiment of a Spinal Stabilization System

Figure 5:
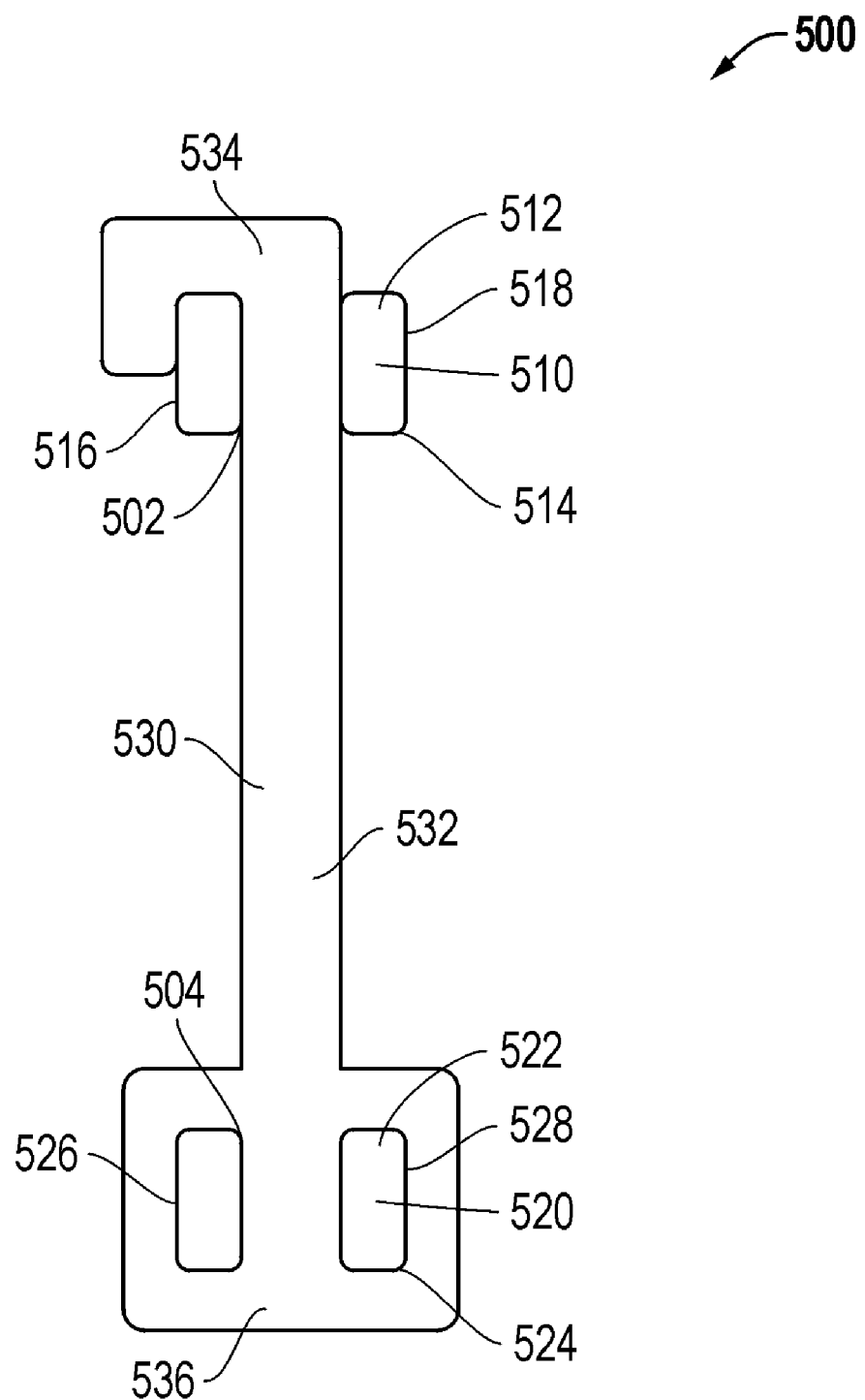
FIG. 5 is a posterior view of a second embodiment of the spinal stabilization system.

Referring to FIG. 5, a second embodiment of a spinal stabilization system is shown and is designated 500. As illustrated, the spinal stabilization system 500 can include a first anchorage component 510 and a second anchorage component 520. In one or more alternative embodiments, the spinal stabilization system 500 can include more than two anchorage components or less than two anchorage components. The anchorage component 510 has a superior end 512 and an inferior end 514 with an axial passage 502 therebetween. Further, the anchorage component 520 has a superior end 522 and an inferior end 524 with an axial passage 504 therebetween. As shown in FIG. 5, the spinal stabilization system 500 can include a surgical rod 530. The surgical rod 530 has an elongate body 532. The elongate body 532 can include a first end 534 and a second end 536. The surgical rod 530 can extend at least partially through each anchorage component 510, 520. In particular, the surgical rod 530 can extend through the axial passage 502, 504 formed in each anchorage component 510, 520.

In an embodiment, the first end 534 of the surgical rod 530 may be adapted to engage at least one face 516, 518 adjacent to the inferior end 514 or the superior end 512 of the anchorage component 510. Further, the second end 536 of the surgical rod 530 may be adapted to engage at least one face 526, 528 adjacent to the inferior end 524 or the superior end 522 of the anchorage component 520. As shown in FIG. 5, the first end 534 of the surgical rod 530 engages the superior end 512 of anchorage component 510 and a side face 516. Alternatively, the second end 536 of surgical rod 530 can engage the superior end 522, the inferior end 524, the entire side face 526, and the entire side face 528 of anchorage component 520 in a wrap-around fashion.

Once the surgical rod 530 is set within the anchorage component 510, 520, the surgical rod 530 can be held in the anchorage component 510, 520 by a fixation component of any suitable configuration (not shown) that extends from each anchorage component 510, 520. In an embodiment, the fixation component allows for translational adjustment of the surgical rod 530. In an embodiment, the fixation component allows for rotational adjustment of the surgical rod 530. In an embodiment, the fixation component irreversibly locks the surgical rod 530 within each respective anchorage component 510, 520. For instance, the fixation component may be a cap, a setscrew, a hoop, or an eyelet. In an embodiment, the hoop allows the surgical rod 530 to slide. In an embodiment, the eyelet is collapsible. In an embodiment, the fixation component is any device that closes the open end of the anchorage component 510, 520 and allows for movement of the surgical rod 530 within the anchorage component 510, 520. In an embodiment, the fixation component is a setscrew where each setscrew can include a break-off head that can be sheared by a break-off tool at a predetermined torque. As such, each setscrew may not be over-torqued.

Description of a Third Embodiment of a Spinal Stabilization System

Figure 6:
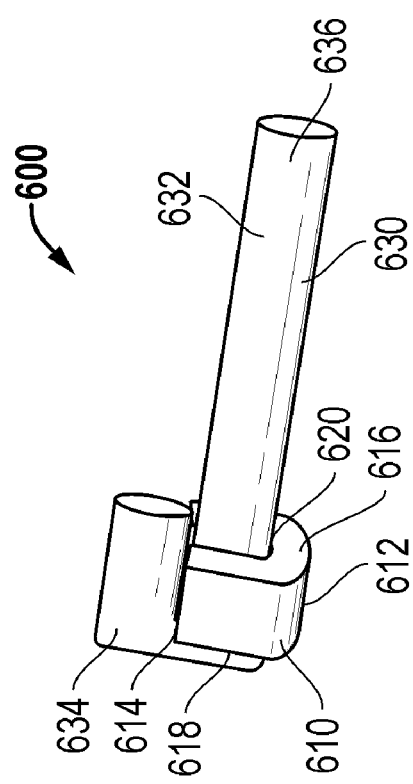
FIG. 6 is a lateral view of a third embodiment of the spinal stabilization system.

Referring to FIG. 6, a third embodiment of spinal stabilization system is shown and is designated 600. In a particular embodiment, the spinal rod 630 can be used in conjunction with multiple anchorage components as described above. As illustrated, the spinal stabilization system 600 includes an anchorage component 610. The anchorage component 610 has a superior end 618 and an inferior end 616 with an axial passage 620 therebetween. As shown in FIG. 6, the spinal stabilization system 600 can include a surgical rod 630. The surgical rod 630 has an elongate body 632. The elongate body 632 can include a first end 634 and a second end 636. The surgical rod 630 can extend at least partially through anchorage component 610. In particular, the surgical rod 630 can extend through the axial passage 620 formed in the anchorage component 610.

In an embodiment, the first end 634 or the second end 636 of the surgical rod 630 may be adapted to engage at least one face 614 adjacent to the inferior end 616 or the superior end 618 of the anchorage component 610. For directional orientation and as seen in FIG. 6, the anchorage component 610 has an anterior end 612 which is in direct contact with and engages the spine (not shown) and a posterior end 614 that is opposite the anterior end 612. In an embodiment, the first end 634 or the second end 636 of the surgical rod 630 is adapted to engage the posterior face 614 as well as the superior end 618 of the anchorage component 630. As seen in FIG. 6, the first end 634 of the surgical rod 630 is configured to engage the superior end 618 and the proximal face 614 of the anchorage component 610.

Once the surgical rod 630 is set within the anchorage component 610, the surgical rod 630 can be held in the anchorage component 610 by a fixation component of any suitable configuration (not shown) that extends from each anchorage component 610. In an embodiment, the fixation component allows for translational adjustment of the surgical rod 630. In an embodiment, the fixation component allows for rotational adjustment of the surgical rod 630. In an embodiment, the fixation component irreversibly locks the surgical rod 630 within the anchorage component 610. For instance, the fixation component may be a cap, a setscrew, a hoop, or an eyelet. In an embodiment, the hoop allows the surgical rod 630 to slide. In an embodiment, the eyelet is collapsible. In an embodiment, the fixation component is any device that closes the open end of the anchorage component 610 and allows for movement of the surgical rod 630 within the anchorage component 610. In an embodiment, the fixation component is a setscrew where each setscrew can include a break-off head that can be sheared by a break-off tool at a predetermined torque. As such, each setscrew may not be over-torqued.

Description of a Fourth Embodiment of a Spinal Stabilization System

Figure 7:
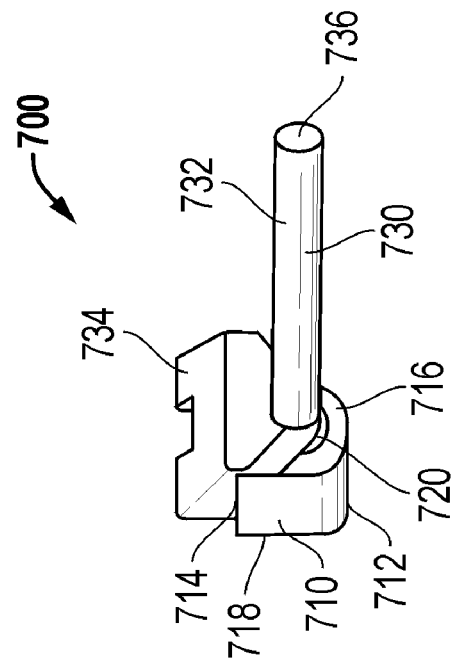
FIG. 7 is a isolateral view of a fourth embodiment of the spinal stabilization system.

Referring to FIG. 7, a fourth embodiment of spinal stabilization system is shown and is designated 700. In a particular embodiment, the spinal rod 730 can be used in conjunction with multiple anchorage components as described above. As illustrated, the spinal stabilization system 700 includes an anchorage component 710. The anchorage component 710 has a superior end 718 and an inferior end 716 with an axial passage 720 therebetween. As shown in FIG. 7, the spinal stabilization system 700 can include a surgical rod 730. The surgical rod 730 has an elongate body 732. The elongate body 732 can include a first end 734 and a second end 736. The surgical rod 730 can extend at least partially through the anchorage component 710. In particular, the surgical rod 730 can extend through the axial passage 720 formed in the anchorage component 710.

In an embodiment, the first end 734 or the second end 736 of the surgical rod 730 may be adapted to engage at least one face 714 adjacent to the inferior end 716 or the superior end 718 of the anchorage component 710. For directional orientation and as seen in FIG. 7, the anchorage component 710 has an anterior end 712 which is in direct contact with and engages the spine (not shown) and a posterior end 714 that is opposite the anterior end 712. In an embodiment, the first end 734 or the second end 736 of the surgical rod 730 is adapted to engage the posterior face 714 as well as the inferior end 716 of the anchorage component. As seen in FIG. 7, the first end 734 of the surgical rod 730 is configured to engage the inferior end 716 and the posterior face 714 of the anchorage component 710.

Once the surgical rod 730 is set within the anchorage component 710, the surgical rod 730 can be held in the anchorage component 710 by a fixation component of any suitable configuration (not shown) that extends from the anchorage component 710. In an embodiment, the fixation component allows for translational adjustment of the surgical rod 730. In an embodiment, the fixation component allows for rotational adjustment of the surgical rod 730. In an embodiment, the fixation component irreversibly locks the surgical rod 730 within the anchorage component 710. For instance, the fixation component may be a cap, a setscrew, a hoop, or an eyelet. In an embodiment, the hoop allows the surgical rod 730 to slide. In an embodiment, the eyelet is collapsible. In an embodiment, the fixation component is any device that closes the open end of the anchorage component 710 and allows for movement of the surgical rod 730 within the anchorage component 710. In an embodiment, the fixation component is a setscrew where each setscrew can include a break-off head that can be sheared by a break-off tool at a predetermined torque. As such, each setscrew may not be over-torqued.

Description of a Fifth Embodiment of a Spinal Stabilization System

Figure 8:
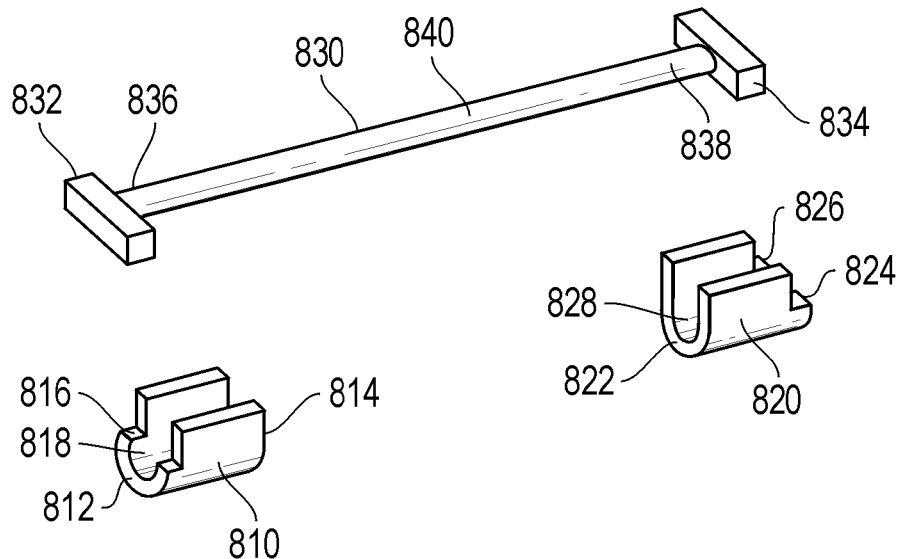
FIG. 8 is a side view of a fifth embodiment of the spinal stabilization system.

Referring to FIG. 8, a fifth embodiment of a spinal stabilization system is shown and is designated 800. As illustrated, the spinal stabilization system 800 can include a first anchorage component 810 and a second anchorage component 820. In one or more alternative embodiments, the spinal stabilization system 800 can include more than two anchorage components or less than two anchorage components. As seen in FIG. 8, the anchorage component 810 has a superior end 812 and an inferior end 814 with an axial passage 818 therebetween. Further, the anchorage component 820 has a superior end 822 and an inferior end 824 with an axial passage 828 therebetween.

As shown in FIG. 8, the spinal stabilization system 800 can include a surgical rod 830. The surgical rod 830 has an elongate body 840. The elongate body 840 can include a first end 836 and a second end 838. The first end 836 has an engagement member 832 that is perpendicular to the axis of the elongate body 840 to engage the anchorage component 810. The second end 838 has an engagement member 834 that is perpendicular to the axis of the elongate body 840 to engage the anchorage component 820. The surgical rod 830 can extend at least partially through each anchorage component 810, 820. In particular, the surgical rod 830 can extend through the axial passage 818, 828 formed in each anchorage component 810, 820.

As seen in FIG. 8, the anchorage component 810, 820 may include further features configured to engage the surgical rod 830. Particularly, the anchorage component 810, 820 may be configured to allow a nested arrangement of the engagement member 832, 834 of the surgical rod 830 when engaging the superior end 812, 822 or the inferior end 814, 824 of the anchorage component 830. The superior ends 812, 822 or the inferior ends 814, 824 can further include a shelf 816, 826 adapted to engage the surgical rod 830. Anchorage component 810 has a shelf 816 on its superior end 812 adapted to engage complimentary engagement member 832. Anchorage component 820 has a shelf 826 on its inferior end 824 adapted to engage complimentary engagement member 834. In an embodiment, the shelf 816, 826 has a seated plane parallel to the plane of the proximal face of anchorage components 810, 820. Alternatively, the shelf 816, 826 may have a seated plane to allow for the surgical rod 830 to sit in any rotational orientation.

Once the surgical rod 830 is set within the anchorage component 810, 820, the surgical rod 830 can be held in the anchorage component 810, 820 by a fixation component of any suitable configuration (not shown) that extends from each anchorage component 810, 820. In an embodiment, the fixation component allows for translational adjustment of the surgical rod 830. In an embodiment, the fixation component allows for rotational adjustment of the surgical rod 830. In an embodiment, the fixation component irreversibly locks the surgical rod 830 within each respective anchorage component 810, 820. For instance, the fixation component may be a cap, a setscrew, a hoop, or an eyelet. In an embodiment, the hoop allows the surgical rod 830 to slide. In an embodiment, the eyelet is collapsible. In an embodiment, the fixation component is any device that closes the open end of the anchorage component 810, 820 and allows for movement of the surgical rod 830 within the anchorage component 810, 820. In an embodiment, the fixation component is a setscrew where each setscrew can include a break-off head that can be sheared by a break-off tool at a predetermined torque. As such, each setscrew may not be over-torqued.

Description of a Sixth Embodiment of a Spinal Stabilization System

Figure 9:
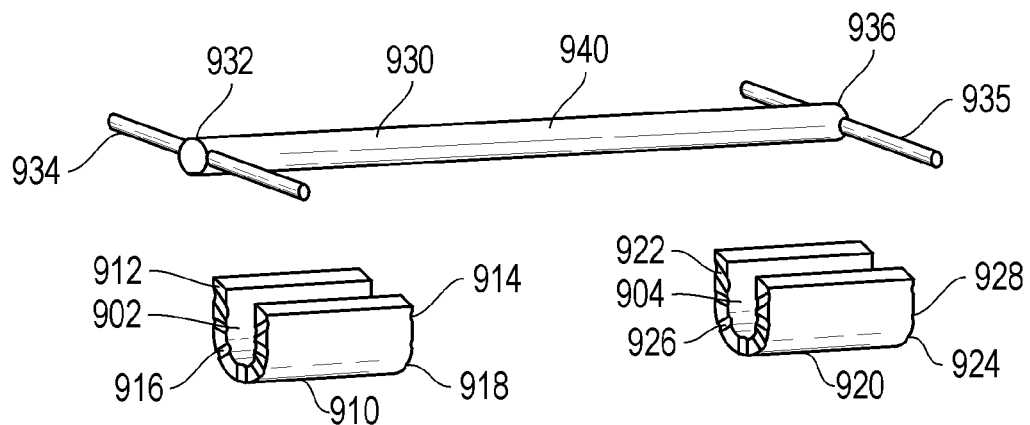
FIG. 9 is a side view of a sixth embodiment of the spinal stabilization system.

Referring to FIG. 9, a sixth embodiment of a spinal stabilization system is shown and is designated 900. As illustrated, the spinal stabilization system 900 can include a first anchorage component 910 and a second anchorage component 920. In one or more alternative embodiments, the spinal stabilization system 900 can include more than two anchorage components or less than two anchorage components. As seen in FIG. 9, the anchorage component 910 has a superior end 912 and an inferior end 914 with an axial passage 902 therebetween. Further, the anchorage component 920 has a superior end 922 and an inferior end 924 with an axial passage 904 therebetween.

As shown in FIG. 9, the spinal stabilization system 900 can include a surgical rod 930. The surgical rod 930 has an elongate body 940. The elongate body 940 can include a first end 932 and a second end 936. The first end 932 has an engagement member 934 that is perpendicular to the axis of the elongate body 940 to engage the anchorage component 910. The second end 936 has an engagement member 938 that is perpendicular to the axis of the elongate body 940 to engage the anchorage component 920. The surgical rod 930 can extend at least partially through each anchorage component 910, 920. In particular, the surgical rod 930 can extend through the axial passage 902, 904 formed in each respective anchorage component 910, 920.

As seen in FIG. 9, the anchorage component 910, 920 may include further features configured to engage the surgical rod 930. Particularly, the anchorage component 910, 920 may be configured to allow a nested arrangement of the engagement member 934, 938 of the surgical rod 930 when engaging the superior end 912, 922 or the inferior end 914, 924 of the anchorage component 910, 920. Anchorage component 910, 920 may include troughs or channels 916, 926 along the superior end 912, 922 adapted to engage complimentary engagement member 934, 938. In an embodiment, the anchorage component 910, 920 may also include troughs or channels 918, 928 along the inferior end 914, 924 adapted to engage the complimentary engagement member 934, 938. The superior end 912, 922 or the inferior end 914, 924 may include one channel or multiple channels with variable angular orientation such that the surgical rod 930 can be set in a variable rotational orientation within the anchorage components 910, 920. The included features of the anchorage components in FIG. 9 allow the surgical rod 930 engage the anchorage components 910, 920 in a seated configuration.

Once the surgical rod 930 is set within the anchorage component 910, 920, the surgical rod 930 can be held in the anchorage component 910, 920 by a fixation component of any suitable configuration (not shown) that extends from each anchorage component 910, 920. In an embodiment, the fixation component allows for translational adjustment of the surgical rod 930. In an embodiment, the fixation component allows for rotational adjustment of the surgical rod 930. In an embodiment, the fixation component irreversibly locks the surgical rod 930 within the respective anchorage components 910, 920. For instance, the fixation component may be a cap, a setscrew, a hoop, or an eyelet. In an embodiment, the hoop allows the surgical rod 930 to slide. In an embodiment, the eyelet is collapsible. In an embodiment, the fixation component is any device that closes the open end of the anchorage component 910, 920 and allows for movement of the surgical rod 930 within the anchorage component 910, 920. In an embodiment, the fixation component is a setscrew where each setscrew can include a break-off head that can be sheared by a break-off tool at a predetermined torque. As such, each setscrew may not be over-torqued.

Description of a Seventh Embodiment of a Spinal Stabilization System

Figure 10:
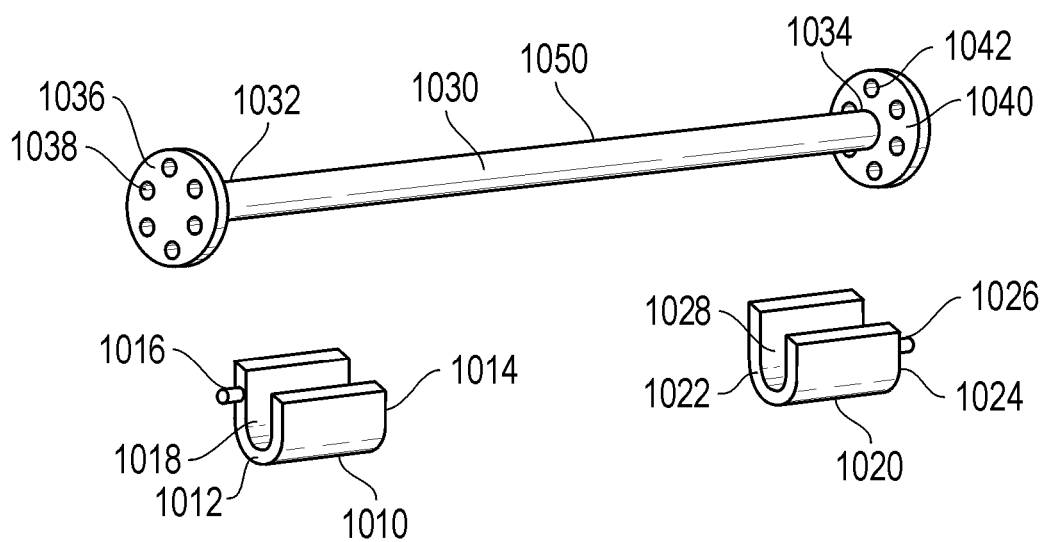
FIG. 10 is a side view of a seventh embodiment of the spinal stabilization system.

Referring to FIG. 10, a seventh embodiment of a spinal stabilization system is shown and is designated 1000. As illustrated, the spinal stabilization system 1000 can include a first anchorage component 1010 and a second anchorage component 1020. In one or more alternative embodiments, the spinal stabilization system 1000 can include more than two anchorage components or less than two anchorage components. As seen in FIG. 10, the anchorage component 1010 has a superior end 1012 and an inferior end 1014 with an axial passage 1018 therebetween. Further, the anchorage component 1020 has a superior end 1022 and an inferior end 1024 with an axial passage 1028 therebetween.

As shown in FIG. 10, the spinal stabilization system 1000 can include a surgical rod 1030. The surgical rod 1030 has an elongate body 1050. The elongate body 1050 can include a first end 1032 and a second end 1034. The first end 1032 has an engagement member 1036 that is perpendicular to the axis of the elongate body 1050 to engage the anchorage component 1010. The second end 1034 has an engagement member 1040 that is perpendicular to the axis of the elongate body 1050 to engage the anchorage component 1020. The surgical rod 1030 can extend at least partially through each anchorage component 1010, 1020. In particular, the surgical rod 1030 can extend through the axial passage 1018, 1028 formed in each anchorage component 1010, 1020.

In this embodiment, the anchorage components 1010, 1020 and the surgical rod 1030 may each include features that correspondingly engage. Particularly, the anchorage components 1010, 1020 may be configured to allow a nested arrangement of the engagement members 1036, 1040 of the surgical rod 1030 when engaging the superior end 1012, 1022 or the inferior end 1014, 1024 of the anchorage component 1010, 1020. The superior ends 1012, 1022 or inferior ends 1014, 1024 of the anchorage components 1010, 1020 may include a peg 1016, 1026 or multiple pegs adapted to engage the surgical rod 1030. The peg 1016, 1026 may be of any suitable configuration to engage the surgical rod 1030. Additionally, the peg 1016, 1026 may be oriented in any position along the superior end 1012, 1022 or inferior end 1014, 1024 of anchorage components 1010, 1020. For instance, anchorage component 1010 has a peg 1016 on its superior end 1012 adapted to engage complimentary engagement member 1036. Anchorage component 1020 has a peg 1026 on its inferior end 1024 adapted to engage complimentary engagement member 1040.

Additionally, the engagement member 1036, 1040 of the surgical rod 1030 may be configured to facilitate the nested arrangement of the engagement member 1036, 1040 within the complimentary anchorage component 1010, 1020. Any suitable configuration of the engagement member 1036, 1040 is envisioned to engage the pegs 1016, 1026. As illustrated, the engagement member 1036, 1040 is configured as a plate containing at least one hole 1038, 1042. The holes 1038, 1042 are adapted to engage the pegs 1016, 1026 in a mating fit. The configuration of the pegs 1016, 1026 and holes 1038, 1042 prevent the surgical rod 1030 from moving rotationally or translationally within the anchorage components 1010, 1020.

Once the surgical rod 1030 is set within the anchorage component 1010, 1020, the surgical rod 1030 can be held in the anchorage component 1010, 1020 by a fixation component of any suitable configuration (not shown) that extends from each anchorage component 1010, 1020. In an embodiment, the fixation component allows for translational adjustment of the surgical rod 1030. In an embodiment, the fixation component allows for rotational adjustment of the surgical rod 1030. In an embodiment, the fixation component irreversibly locks the surgical rod 1030 within the anchorage component 1010, 1020. For instance, the fixation component may be a cap, a setscrew, a hoop, or an eyelet. In an embodiment, the hoop allows the surgical rod 1030 to slide. In an embodiment, the eyelet is collapsible. In an embodiment, the fixation component is any device that closes the open end of the anchorage component 1010, 1020 and allows for movement of the surgical rod 1030 within the anchorage component 1010, 1020. In an embodiment, the fixation component is a setscrew where each setscrew can include a break-off head that can be sheared by a break-off tool at a predetermined torque. As such, each setscrew may not be over-torqued.

Description of an Eighth Embodiment of a Spinal Stabilization System

Figure 11:
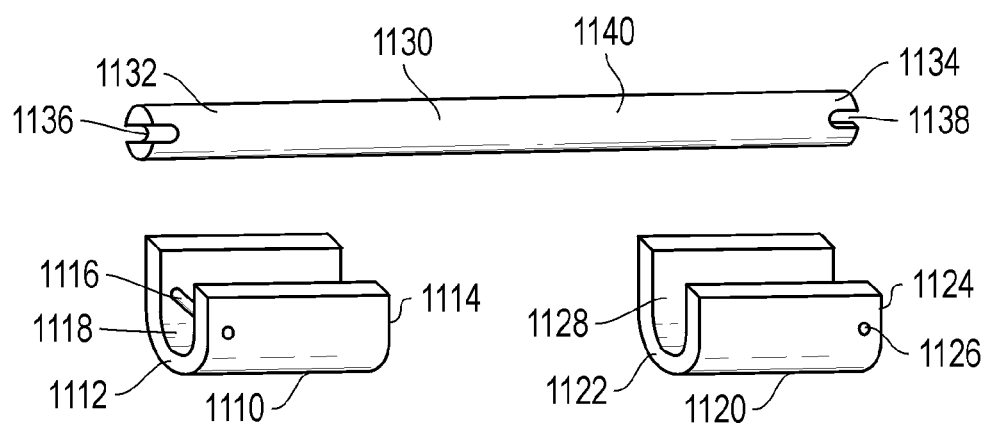
FIG. 11 is a side view of an eighth embodiment of the spinal stabilization system.

Referring to FIG. 11, an eighth embodiment of a spinal stabilization system is shown and is designated 1100. As illustrated, the spinal stabilization system 1100 can include a first anchorage component 1110 and a second anchorage component 1120. In one or more alternative embodiments, the spinal stabilization system 1100 can include more than two anchorage components or less than two anchorage components. As seen in FIG. 11, the anchorage component 1110 has a superior end 1112 and an inferior end 1114 with an axial passage 1118 therebetween. Further, the anchorage component 1120 has a superior end 1122 and an inferior end 1124 with an axial passage 1128 therebetween.

As shown in FIG. 11, the spinal stabilization system 1100 can include a surgical rod 1130. The surgical rod 1130 has an elongate body 1140. The elongate body 1140 can include a first end 1132 and a second end 1134. The first end 1132 has an engagement member 1136 to engage the anchorage component 1110. The second end 1134 has an engagement member 1138 to engage the anchorage component 1120. The surgical rod 1130 can extend at least partially through each anchorage component 1110, 1120. In particular, the surgical rod 1130 can extend through the axial passage 1118, 1128 formed in each anchorage component 1110, 1120.

In this embodiment, the anchorage components 1110, 1120 and the surgical rod 1130 may each include features to correspondingly engage. Particularly, the anchorage components 1110, 1120 may be configured to allow a nested arrangement of the engagement member 1136, 1138 of the surgical rod 1130 when engaging the superior end 1112, 1122 or the inferior end 1114, 1124 of the anchorage component 1110, 1120. Included within the axial passage 1118, 1128 of the respective anchorage components 1110, 1120 are a pin 1116, 1126 that transverses the axial passage 1118, 1128 to engage the surgical rod 1130. The pin 1116, 1126 may be shaped in any suitable configuration to engage the surgical rod 1130. Additionally, the pin 1116, 1126 may be translationally oriented in any position along the axial passage 1118, 1128 of anchorage components 1110, 1120. The pin 116, 1126 may be oriented along the superior end 1112, 1122 of the anchorage component 1110, 1120 or along the inferior end 1114, 1124 of the anchorage component 1110, 1120. As illustrated, the pin 1116, 1126 transverses the axial passage 1118, 1128 in a plane that is parallel to the plane of the proximal face of anchorage components 1110 and 1120. Alternatively, the pins 1116, 1126 may transverse the axial passage 1118, 1128 in any plane to allow for the surgical rod 1130 to sit in any rotational orientation within the anchorage component 1110, 1120.

Additionally, the engagement member 1136, 1138 of the surgical rod 1130 may be configured to facilitate the nested arrangement of the engagement member 1136, 1138 within the complimentary anchorage component 1110, 1120. Any suitable configuration of the complimentary engagement members 1136, 1138 is envisioned to engage the pins 1116, 1126. As illustrated, the engagement member 1136, 1138 is configured as a channel to engage the pins 1116, 1126. The channels 1136, 1138 are adapted to engage the pins 1116, 1126 in a mating fit. The configuration of the pins 1116, 1126 and channels 1136, 1138 prevent the surgical rod from moving rotationally or translationally within the anchorage components 1110, 1120.

Once the surgical rod 1130 is set within the anchorage component 1110, 1120, the surgical rod 1130 can be held in the anchorage component 1110, 1120 by a fixation component of any suitable configuration (not shown) that extends from each anchorage component 1110, 1120. In an embodiment, the fixation component allows for translational adjustment of the surgical rod 1130. In an embodiment, the fixation component allows for rotational adjustment of the surgical rod 1130. In an embodiment, the fixation component irreversibly locks the surgical rod 1130 within the respective anchorage components 1110, 1120. For instance, the fixation component may be a cap, a setscrew, a hoop, or an eyelet. In an embodiment, the hoop allows the surgical rod 1130 to slide. In an embodiment, the eyelet is collapsible. In an embodiment, the fixation component is any device that closes the open end of the anchorage component 1110, 1120 and allows for movement of the surgical rod 1130 within the anchorage component 1110, 1120. In an embodiment, the fixation component is a setscrew where each setscrew can include a break-off head that can be sheared by a break-off tool at a predetermined torque. As such, each setscrew may not be over-torqued.

Description of a Ninth Embodiment of a Spinal Stabilization System

Figure 12:
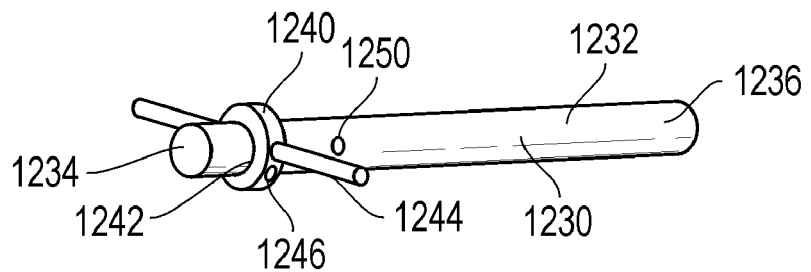
FIG. 12 is a side view of a ninth embodiment of the engagement member and surgical rod of the spinal stabilization system.

Referring to FIG. 12, a ninth embodiment of a surgical rod 1230 is shown. The surgical rod 1230 can be used in conjunction with the spinal stabilization systems discussed. The surgical rod 1230 has an elongate body 1232. The elongate body 1232 can include a first end 1234 and a second end 1236. The first end 1234 has an engagement member 1240. As seen in FIG. 12, the engagement member 1240 may be formed as separate pieces and fixed to the surgical rod 1230. For instance, the engagement member 1240 has at least one rod 1244 projecting perpendicularly from the axis of the elongate body 1232 of the surgical rod 1230 to engage a complimentary anchorage component. Further, the engagement member 1240 has an aperture 1242 configured to engage the surgical rod 1230. Dimensions for the aperture 1242 include any shape that can fit a complimentary shape on the surgical rod 1230.

As seen in FIG. 12, the aperture 1242 and the surgical rod 1230 may be dimensioned to allow the engagement member 1240 to translate along the surgical rod 1230. The aperture 1242 and the surgical rod 1230 may also be dimensioned to allow the engagement member 1240 to rotate along the surgical rod 1230. The aperture 1242 has a round cross-section. At least one end 1234, 1236 of the surgical rod 1230 has a complimentary round cross-section to engage the aperture 1242. In an embodiment, the surgical rod 1230 may also include stop members 1250 to guide the translational movement of the engagement member 1240 along the surgical rod 1230.

The engagement member 1240 may also include a locking component 1246 to fix the engagement member 1240 to the surgical rod 1230. The locking component 1246 can lock the engagement member 1240 in a rotational orientation. Further, the locking component 1246 can lock the engagement member 1240 in a translational orientation. In an embodiment, the locking component 1246 irreversibly locks the engagement member 1240 to the surgical rod 1230. Alternatively, the locking component 1246 can temporarily lock the engagement member 1240 to the surgical rod 1230. The locking component 1246 may be a setscrew. The engagement member 1240 further includes complimentary holes sized and shaped to receive the locking component. In an embodiment, the engagement member 1240 includes threaded holes to receive the setscrew.

Description of a Tenth Embodiment of a Spinal Stabilization System

Figure 13:
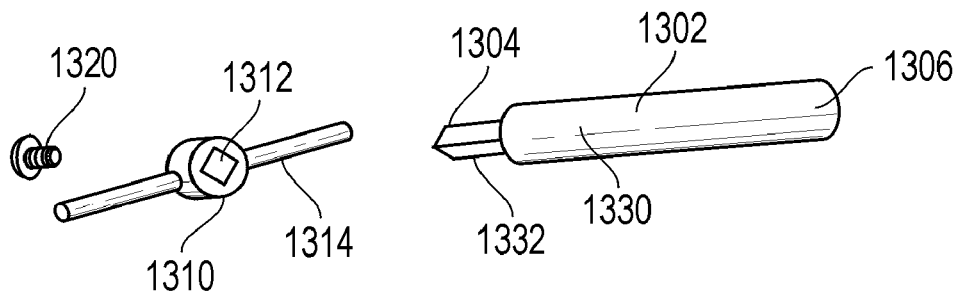
FIG. 13 is a side view of a tenth embodiment of the engagement member and surgical rod of the spinal stabilization system.

Referring to FIG. 13, a tenth embodiment of a surgical rod 1330 is shown. The surgical rod 1330 can be used in conjunction with the spinal stabilization systems discussed. The surgical rod 1330 has an elongate body 1302. The elongate body 1302 can include a first end 1304 and a second end 1306. The first end 1304 has an engagement member 1310. As seen in FIG. 13, the engagement member 1310 may be formed as separate pieces and fixed to the surgical rod 1330. For instance, the engagement member 1310 has at least one rod 1314 projecting perpendicularly from the axis of the elongate body 1302 of the surgical rod 1330 to engage a complimentary anchorage component. Further, the engagement member 1310 has an aperture 1312 configured to engage the surgical rod 1330. Dimensions for the aperture 1310 include any shape that can fit a complimentary shape on the surgical rod 1330.

The aperture 1312 and the surgical rod 1330 may be dimensioned to allow the engagement member 1310 to translate along the surgical rod 1330. The aperture 1312 and the surgical rod 1330 may also be dimensioned to allow the engagement member 1310 to be set in a rotational configuration along the surgical rod 1330. For instance, as seen in FIG. 13, the aperture 1312 has a square configuration. At least one end 1304, 1306 of the surgical rod 1330 has a complimentary square cross-section 1332 to engage the aperture 1312.

The engagement member 1310 may further include a locking mechanism 1320 to fix the engagement member 1310 to the surgical rod 1330. The locking component 1320 can lock the engagement member 1310 in a rotational orientation. Further, the locking component 1320 can lock the engagement member 1310 in a translational orientation. In an embodiment, the locking component 1320 irreversibly locks the engagement member 1310 to the surgical rod 1330. Alternatively, the locking component 1320 can temporarily lock the engagement member 1310 to the surgical rod 1330. The locking component 1320 may be a setscrew. The engagement member 1310 further includes complimentary holes sized and shaped to receive the locking component. In an embodiment, the engagement member 1310 includes threaded holes to receive the setscrew.

Description of an Eleventh Embodiment of a Spinal Stabilization System

Figure 14:
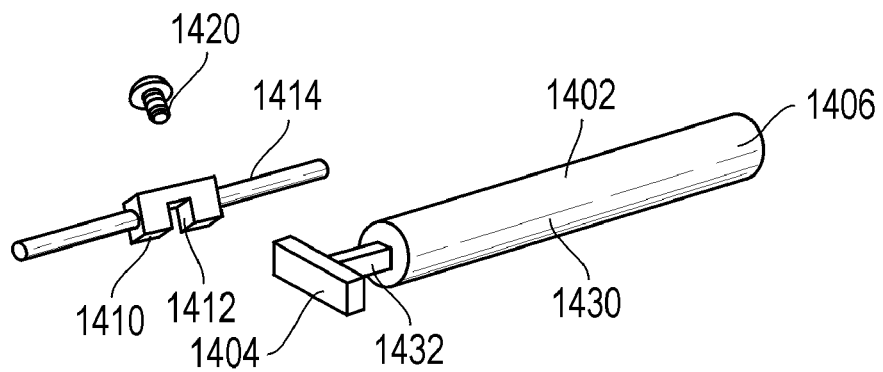
FIG. 14 is a side view of an eleventh embodiment of the engagement member and surgical rod of the spinal stabilization system.

Referring to FIG. 14, an eleventh embodiment of a surgical rod 1430 is shown. The surgical rod 1430 can be used in conjunction with the spinal stabilization systems discussed. The surgical rod 1430 has an elongate body 1402. The elongate body 1402 can include a first end 1404 and a second end 1406. The first end 1404 has an engagement member 1410. As seen in FIG. 14, the engagement member 1410 may be formed as separate pieces and fixed to the surgical rod 1430. For instance, the engagement member 1410 has at least one rod 1414 projecting perpendicularly from the axis of the elongate body 1402 of the surgical rod 1430 to engage a complimentary anchorage component. Further, the engagement member 1410 has an aperture 1412 configured to engage the surgical rod 1430. Dimensions for the aperture 1412 include any shape that can fit a complimentary shape on the surgical rod 1430.

The aperture 1412 and the surgical rod 1430 may be dimensioned to allow the engagement member 1410 to translate along the surgical rod 1430. The aperture 1412 and the surgical rod 1430 may also be dimensioned to allow the engagement member 1410 to be set in a rotational configuration along the surgical rod 1430. As seen in FIG. 14, the aperture 1412 has a horseshoe configuration. At least one end 1404, 1406 of the surgical rod 1430 has a complimentary square cross-section 1432 to engage the aperture 1412.

The engagement member 1410 may further include a locking mechanism 1420 to fix the engagement member 1410 to the surgical rod 1430. The locking component 1420 can lock the engagement member 1410 in a rotational orientation. Further, the locking component 1420 can lock the engagement member 1410 in a translational orientation. In an embodiment, the locking component 1420 irreversibly locks the engagement member 1410 to the surgical rod 1430. Alternatively, the locking component 1420 can temporarily lock the engagement member 1410 to the surgical rod 1430. The locking component 1420 may be a setscrew. The engagement member 1410 further includes complimentary holes sized and shaped to receive the locking component. In an embodiment, the engagement member 1410 includes threaded holes to receive the setscrew.

Description of a Twelfth Embodiment of a Spinal Stabilization System

Figure 15:
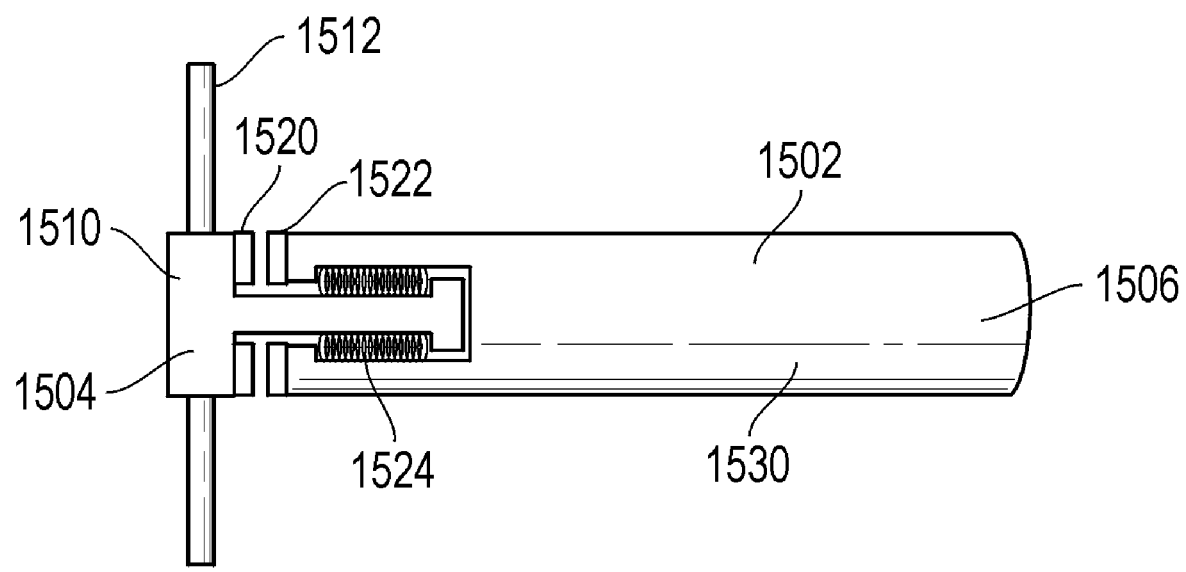
FIG. 15 is a side view of a twelfth embodiment of the engagement member and surgical rod of the spinal stabilization system.

Referring to FIG. 15, a twelfth embodiment of a surgical rod 1530 is shown. The surgical rod 1530 can be used in conjunction with the spinal stabilization systems discussed. The surgical rod 1530 has an elongate body 1502. The elongate body 1502 can include a first end 1504 and a second end 1506. The first end 1504 has an engagement member 1510. As seen in FIG. 15, the engagement member 1510 may be formed as separate pieces and fixed to the surgical rod 1530. An alternative configuration of a locking component can be seen in FIG. 15 that locks the engagement member 1510 in a rotational or translational orientation.

Surgical rod 1530 includes engagement member 1510 with rods 1512 projecting perpendicularly from surgical rod 1530 to engage a complimentary anchorage component. Engagement member 1510 includes a first spline 1520 configured to engage a complimentary second spline 1522 in a face-to-face engagement. The engagement of first spline 1520 with complimentary second spline 1522 locks the engagement member 1510 to the surgical rod 1530. The splines 1520, 1522 allow the engagement member 1510 to be fixed in a specific rotational orientation. The splines 1520, 1522 may also allow the engagement member 1510 to be fixed in a specific translational orientation. Further, the engagement member 1510 may include springs 1524 configured to engage and disengage the first spline 1520 and the complimentary second spline 1522 to adjust the rotational orientation and translational orientation of the surgical rod 1530 in the complimentary anchorage component.

Description of a Method of Treating a Spine

Figure 16:
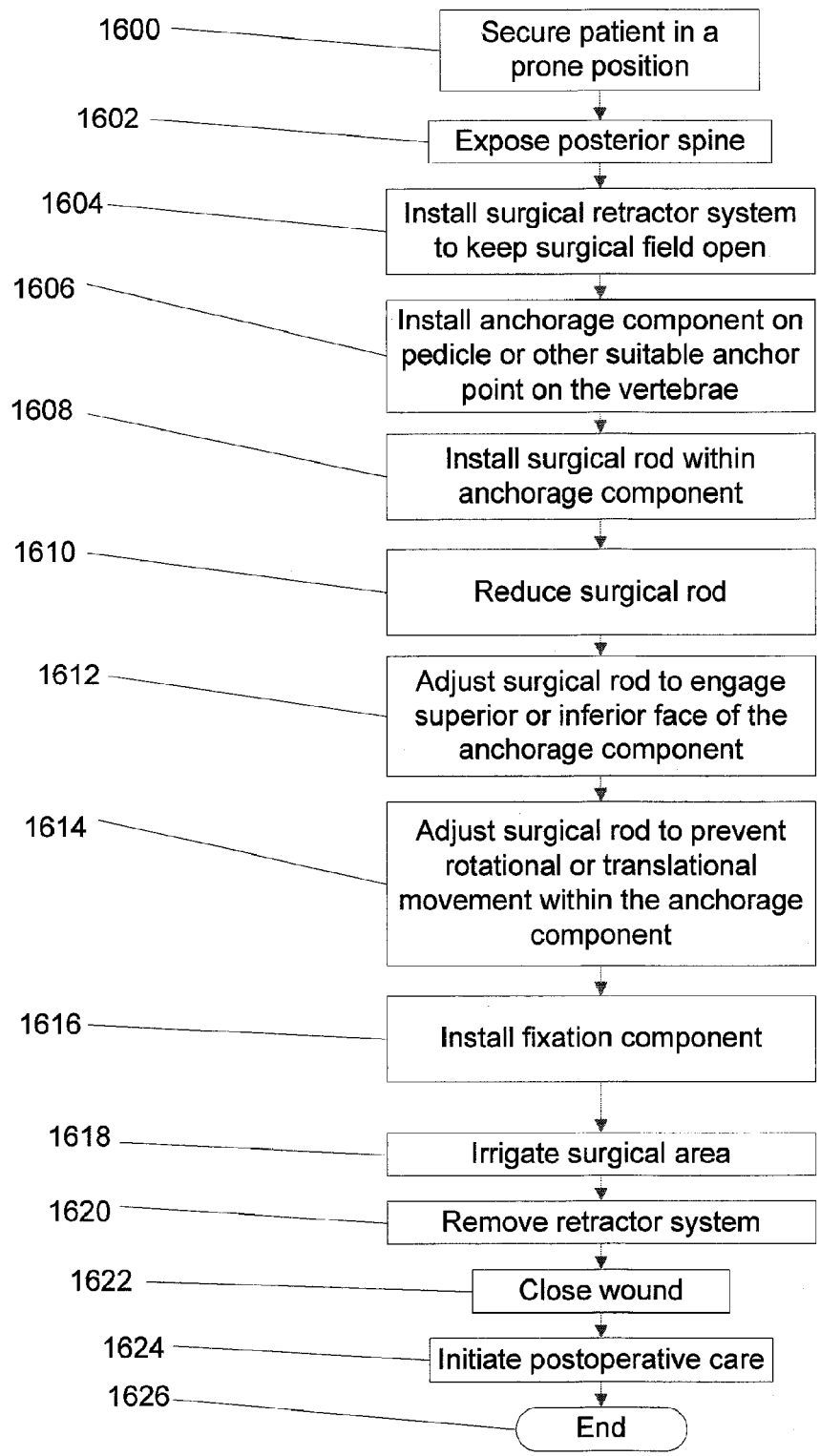
FIG. 16 is a flow chart illustrating a method of installing a spinal stabilization system.

Referring to FIG. 16, an exemplary, non-limiting embodiment of a method of treating a spine is shown and commences at block 1600. At block 1600, a patient is secured on an operating table. For example, the patient can be secured in a prone position to allow a posterior approach to be used to access the patient's spinal column.

Moving to block 1602, the surgical area along spinal column is exposed. Further, at block 1604, a surgical retractor system can be installed to keep the surgical field open. For example, the surgical retractor system can be a surgical retractor system configured for posterior access to a spinal column.

Proceeding to block 1606, the anchorage components of the spinal stabilization system can be installed on the pedicle or other suitable anchor point on the vertebrae. Multiple anchorage components, that are similarly configured, can be installed along the spinal column on the pedicle or other suitable anchor point of the adjacent vertebra.

Moving to block 1608, a surgical rod can be installed along the anchorage components so that the surgical rod is within or near an axial passage formed in each anchorage component. At block 1610, the surgical rod can be reduced. In other words, a tool, e.g., a reducer, an approximator, an introducer, a persuader, or a combination thereof, can be used to move the surgical rod into the axial passage formed in each anchorage component. At block 1612, surgical rod is adjusted to engage the superior end or the inferior end of the anchorage component. At block 1614, the surgical rod is adjusted to substantially constrain rotational movement or translational movement within the anchorage component. This may include locking a locking component such as setscrews on the engagement member to secure the engagement member to the surgical rod. In an embodiment, this may include adjusting the engagement member to engage at least one face adjacent to the inferior end or the superior end of the anchorage component.

At block 1616, fixation components can be installed within each anchorage component, e.g., setscrews within a threaded hole. The setscrews can hold the surgical rod in place relative to each anchorage component of the spinal stabilization system. Installing the fixation component can include tightening each setscrew, e.g., using a nut driver or other similar tool. Further, each setscrew can be torqued using a break-off tool in order to shear a break-off cap of each setscrew. This can ensure that each setscrew is torqued to approximately the same torque value.

At block 1618, the intervertebral space can be irrigated. Further, at block 1620, the retractor system can be removed. At block 1622, the surgical wound can be closed. The surgical wound can be closed using sutures, surgical staples, or any other surgical technique well known in the art. Moving to block 1624, postoperative care can be initiated. The method can end at state 1626.

CONCLUSION

With the configuration of structure described above, the spinal stabilization system provides a device that may be implanted to support or stabilize at least a portion of a spinal column that is diseased, degenerated, or otherwise damaged. Further, the surgical rod can be installed in a rotational orientation or translational orientation along the anchorage components to provide support and stability for the spinal column. By orienting the surgical rod in within the anchorage components, the surgical rod can be custom tailored for the spine. As such, spinal fixation using the surgical rods described herein can be very effective to correct spinal defects.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. component.

What is claimed is:

1. A spinal stabilization system comprising:
   at least one anchorage component having a superior end, an inferior end, and an axial passage therebetween; and
   a surgical rod configured to be installed at least partially within the axial passage of the anchorage component wherein the surgical rod comprises an elongate body having a first end and a second end and defines a longitudinal axis wherein the first end is adapted to engage the superior end or the inferior end of a first anchorage component and the second end is configured to engage the superior end and the inferior end of a second anchorage component to substantially constrain rotational movement of the surgical rod within the anchorage component.

2. The spinal stabilization system of claim 1, wherein the surgical rod engages the anchorage component in a configuration to substantially constrain translational movement of the surgical rod within the anchorage component.

3. The spinal stabilization system of claim 1, wherein the superior end and/or the inferior end of the anchorage component includes a shelf adapted to engage the rod member of the surgical rod.

4. The spinal stabilization system of claim 1, wherein the superior end and/or the inferior end of the anchorage component includes at least one channel adapted for fixation with the rod member of the surgical rod.

5. The spinal stabilization system of claim 1, wherein the superior end and/or the inferior end of the anchorage component includes at least one peg, and the first end and/or second end of the surgical rod includes a plate perpendicular to the axis of the elongate body, wherein the plate has at least one hole adapted to engage the peg.

6. The spinal stabilization system of claim 1, wherein the surgical rod is further adapted to engage at least one face adjacent to the inferior end and/or the superior end of the anchorage component.

7. The spinal stabilization system of claim 1, wherein the first end and/or the second end of the surgical rod is adapted to engage the superior end and/or the inferior end of the anchorage component is at least partially formed of shape-memory material.

8. The spinal stabilization system of claim 1, wherein the rod member has at least one rod projecting perpendicular to the axis of the elongate body of the surgical rod and the anchorage component has an aperture configured to engage the surgical rod.

9. The spinal stabilization system of claim 8, wherein the rod member further includes a locking component.

10. A surgical rod comprising:
    an elongate body having a distal end, a proximal end and defining a longitudinal axis; and
    an elongated rod member disposed substantially perpendicular to the longitudinal axis of the elongate body, wherein the elongated rod member extends from an outer surface of the elongate body and is fixedly disposed at the distal end and the proximal end of the elongate body and the elongate body disposed at the proximal end is configured for fixation with a superior end or an inferior end of a first anchorage component and the elongate body disposed at the distal end is configured to engage a superior end and an inferior end of a second anchorage component to substantially constrain rotational movement of the surgical rod within the anchorage component.

11. The surgical rod of claim 10, wherein the elongated rod member is configured to substantially constrain translational movement of the elongate body within the anchorage component.

12. The surgical rod of claim 10, wherein the elongated rod member is configured to translate or rotate with the elongate body.

13. The surgical rod of claim 10, wherein the elongated rod member is at least partially formed of shape-memory material.

14. The surgical rod of claim 13, wherein the shape-memory material is Nitinol.

15. The surgical rod of claim 10, wherein the elongate body comprises a substantially rigid biocompatible material, comprising a polyaryletherketone (PAEK) material.

16. The surgical rod of claim 15, wherein the polyaryletherketone material comprises polyetherketone (PEK), polyetheretherketone (PEEK), polyetherketoneketone (PEKK), polyetherketoneetherketoneketone (PEKEKK), or a combination thereof.

17. The surgical rod of claim 10, wherein the elongated rod member further includes a locking component to secure the elongated rod member to the surgical rod.

18. A method of treating a spine, comprising:
    installing a first anchorage component on a first vertebra, the first anchorage component having a superior end and an inferior end;
    installing a surgical rod within the superior or the inferior end of the first anchorage component, the surgical rod defining a longitudinal axis and including an elongated rod member disposed substantially perpendicular to the longitudinal axis, the rod member extending from an outer surface of a proximal end or a distal end of the surgical rod and being fixedly disposed at the proximal end or the distal end in a configuration for fixation with the first anchorage component;
    adjusting the surgical rod to engage the superior end or the inferior end of the first anchorage component;
    adjusting the surgical rod such that the rod member is fixed with the first anchorage component to substantially constrain rotational movement of the surgical rod within the first anchorage component;
    installing a second anchorage component having a superior end and an inferior end on a second vertebra of the spinal column;
    installing the surgical rod with the superior and the inferior end of the second anchorage component;
    adjusting the surgical rod to engage the superior end or the inferior end of the second anchorage component; and
    adjusting the surgical rod to substantially constrain rotational movement of the surgical rod within the second anchorage component.

19. The method of claim 18, further comprising adjusting the surgical rod to substantially constrain translational movement of the surgical rod within the first anchorage component.

20. The method of claim 18, further comprising adjusting the surgical rod to substantially constrain translational movement of the surgical rod within the second anchorage component.

21. The method of claim 18, further comprising:
    installing a first set screw in the first anchorage component to secure the surgical rod therein; and
    installing a second set screw in the second anchorage component to secure the surgical rod therein.

22. A kit, comprising:
    a plurality of anchorage components having a superior end, an inferior end, and an axial passage therebetween;
    a surgical rod configured to be installed within each of the plurality of anchorage components, the surgical rod defining a longitudinal axis and having an elongated rod member disposed substantially perpendicular to the longitudinal axis, the rod member extending from a proximal end and a distal end of an outer surface of the surgical rod the rod disposed at the proximal end is configured for fixation with the superior end or an inferior end of a first anchorage component and the rod disposed at the distal end is configured to engage the superior end and the inferior end of a second anchorage component to substantially constrain rotational movement of the surgical rod within the anchorage components; and
    a plurality of set screws configured to secure the surgical rod within each of the plurality of anchorage components.

* * * * *